(12) United States Patent
Corazzari et al.

(10) Patent No.: US 10,617,810 B2
(45) Date of Patent: Apr. 14, 2020

(54) LIGHT SHIELD FOR SENSOR AND DISPOSABLE KIT PROVIDED THEREWITH

(71) Applicant: B. BRAUN AVITUM AG, Melsungen (DE)

(72) Inventors: Enrico Corazzari, Modena (IT); Botond Tényi, Budapest (HU); Máté Bocz, Budapest (HU); Jörn Ahrens, Baunatal (DE)

(73) Assignee: B. Braun Avitum AG, Melsungen (DE)

( * ) Notice: Subject to any disclaimer, the term of this patent is extended or adjusted under 35 U.S.C. 154(b) by 333 days.

(21) Appl. No.: 15/490,188

(22) Filed: Apr. 18, 2017

(65) Prior Publication Data

US 2017/0299499 A1 Oct. 19, 2017

(30) Foreign Application Priority Data

Apr. 18, 2016 (EP) ..................................... 16165845

(51) Int. Cl.
*A61M 1/16* (2006.01)
*G01N 21/03* (2006.01)
(Continued)

(52) U.S. Cl.
CPC ....... *A61M 1/1692* (2013.01); *G01N 21/0303* (2013.01); *G01N 21/59* (2013.01);
(Continued)

(58) Field of Classification Search
CPC ........ A61M 1/1692; A61M 2205/3306; G01N 21/0303; G01N 21/85
See application file for complete search history.

(56) References Cited

U.S. PATENT DOCUMENTS 4,136,818 A 1/1979 Larrabee
4,181,610 A 1/1980 Shintani et al.
(Continued)

OTHER PUBLICATIONS

European Search Report (translation) for EP 16165845.5 dated Oct. 24, 2016.
(Continued)

*Primary Examiner* — Leslie R Deak
(74) *Attorney, Agent, or Firm* — RatnerPrestia

(57) ABSTRACT

A light shield is arranged in a light shielding position with respect to a sensor or a blood leakage detector installed in a medical apparatus and monitoring for changes of transmittance in a translucent fluid carried in a tubing connected to the medical apparatus. The light shield has a non-transparent configuration and is configured to prevent environmental light from being incident on a relevant detection active sensor area. Further, a disposable kit for a medical apparatus which is arranged to be mounted to the medical apparatus and to carry pre-installed disposables to be used during a medical treatment comprises a hard-shell subassembly arranged to be positioned in a region of the medical apparatus in the vicinity of a detection active sensor area of a sensor which is sensitive to light and installed in the medical apparatus. At least one light shield element is selected from first to third light shield elements, and the at least one light shield element is mounted to the hard-shell subassembly of the disposable kit in a region where the detection active sensor area is underneath.

14 Claims, 2 Drawing Sheets

(51) Int. Cl.
*G01N 21/85* (2006.01)
*G01N 21/59* (2006.01)
*G01N 33/49* (2006.01)

(52) U.S. Cl.
CPC ............ *G01N 21/85* (2013.01); *G01N 33/49* (2013.01); *A61M 2205/0238* (2013.01); *A61M 2205/3306* (2013.01); *G01N 2201/0646* (2013.01)

(56) References Cited

U.S. PATENT DOCUMENTS

| | | |
|---|---|---|
| 10,130,749 B2 * | 11/2018 | Schade ................. A61M 1/367 |
| 2003/0210390 A1 | 11/2003 | O'Mahony et al. |
| 2007/0239096 A1 | 10/2007 | Keenan et al. |
| 2009/0012454 A1 | 1/2009 | Childers |
| 2010/0094192 A1 | 4/2010 | Peters et al. |

OTHER PUBLICATIONS

"Clamp Components," Hoses Direct online catalogue, www.hoses.co.uk, Apr. 29, 2015, p. 811.

* cited by examiner

LIGHT SHIELD FOR SENSOR AND DISPOSABLE KIT PROVIDED THEREWITH

CROSS REFERENCE TO RELATED APPLICATIONS

This application claims priority to European application EP 16 165 845.5 filed Apr. 18, 2016, the contents of such application being incorporated by reference herein.

FIELD OF THE INVENTION

The invention relates to a light shield for an optical sensor monitoring a fluid carried in a tubing in a medical apparatus and to a pre-assembled disposable kit or packaging for a medical apparatus comprising the light shield within the disposable.

BACKGROUND OF THE INVENTION

During a dialysis treatment a filter with a semi-permeable membrane is used to remove substances from the patient and control the patient weight. This semi-permeable membrane is dividing the dialysate side and the blood side. Blood cells are not able to pass such a semi-permeable membrane as long as there are no ruptures of the fibers.

In case of a membrane rupture it is possible that not only plasma but also blood cells are passing the membrane to the dialysate side. This is dangerous for the patient and so a standard measure to detect such ruptures is to position an optical sensor (blood leak detector) at the outlet of the dialysis fluid/ultrafiltration fluid in order to detect blood diluted inside the line as early as possible and provide alarm to staff for evaluation.

State of the art blood leak detectors measure the absorbance of different light spectra in the visible range. Intrusion of environmental light in same range can impact and affect the measurement method and cause false alarms.

Known approaches to these problems combine a tube and sensor fixed inside a dialysis device, employ a sensor having a cover door on the sensor itself which need to be open and closed for tube loading, or use high sided arrangements in order to reduce a total impact caused by foreign light.

The aforementioned issue is largely irrelevant for integrated sensors inside dialysis devices where it is not part of the disposable set but integrated in the device fluid path. If, however, a sensor is mounted on a surface outside the housing environmental light has a relevant impact. Approaches like inserting tubing and opening/closing a cover door to protect against environmental light have the severe disadvantage that manual steps are required, and that an automatic insertion of multiple tubing at a same time and a usage of such cover is not possible. Besides, a tube fixedly integrated into the sensor is does not allow for the usage of a disposable set as an exchangeable part.

In a pre-assembled disposable kit, where ail the bloodline and the filters are fixed on a holder, the holder has the aim and purpose to facilitate and speed up the setup of the kit on the machine. This is key important for the user to improve usability and speed while avoiding mistakes. Therefore, some tube portion of the kit must fit directly into the machine sensor during the loading of the kit, for instance the BLD (Blood Leak detector), without any additional cover.

SUMMARY OF THE INVENTION

In view of the above, an object of the invention resides in providing a sensor shield preventing environmental light in the same wavelength range as that of a sensor from being incident onto the sensor.

In addition, the invention shall provide a disposable kit for a medical apparatus comprising such a sensor shield.

According to aspects of the present invention, this object is accomplished by a sensor shield and by a disposable kit for a medical apparatus as defined in the claims.

A general idea underlying the present invention resides in creating a dedicated component mounted on the disposable kit in order to create a "shield" between a sensor and the external environment, and in particular creating a dedicated and non-transparent (sensor and/or sensor surface) shield inside the disposable kit to cover an existing sensor which is mounted on the dialysis device and to protect it against environmental light, and to provide a disposable kit with such a shield (or include such a shield in the disposable kit) so as to provide protection against environmental light without degrading usability advantages such as simple tube insertion and the non-necessity of further manual steps.

According to one aspect, a user is enabled to insert a tubing into a U-shaped optical sensor slot and to automatically cover an area non-transparently without any additional manual step, and thereby protect the sensor from environmental light disturbing the sensor during therapy. Along with this insertion process, also multiple tubes can be inserted at a same time and allow a pre-assembled mounting of a tubing on plate of a disposable kit or set. The latter further allows insertion of multiple tubes fixed to a cassette at a same time, rendering a plug-and-play disposable kit or set.

The above described general idea may, for example, be technically realized by arranging an area or a cover inside the disposable kit which is configured to absorb light and thereby to protect the optical sensor located underneath. In a case in which tubing is already pre-assembled inside the disposable kit, single or plural pre-defined areas can incorporate a cover to protect or shield optical sensors positioned underneath against environmental light.

Example technical configurations may reside in painting a surface area of a tubing that does not touch the light path and shields the sensor from impacts of environmental light, or in placing a non-transparent material (sticker) on a surface area of the tubing does not touch the light path and shields the sensor from impacts of environmental light. It is noted that the painting or non-transparent material may cover as much an area of the tubing as technically possible to thereby allow only an optical path of the sensor to pass.

In other words, the afore-mentioned example technical configurations may include forming a non-transparent area inside the disposable kit or set (or a plate thereof) and/or on tubing, the non-transparent area being configured to absorb light to thereby protect the optical sensor. In cases where tubing, e.g. the entire tubing of the disposable kit, is already pre-assembled inside the disposable kit, single or plural pre-defined areas can be used as a cover and protect optical sensors arranged below or underneath. The cover may be a light absorbing area on the plate, or may be embodied in the form of one or more plastic parts forming part of the disposable kit and covering the optical sensor located underneath.

A further and technically preferable solution resides in protecting the optical sensor with a special, expanded elastomeric material formed to a component in a predetermined manner and positioned behind an optical sensor tube portion in the disposable kit such that the component, after loading of the disposable kit, covers the sensor, thereby avoiding any unwanted influence of external light.

According to aspects of the invention, advantages achieved include for example an automatic protection of an optical sensor without any additional usability/handling steps for a user, an improved reliability of an optical sensor in case of unfavorable environmental light conditions, the possibility of direction/frontal insertion of one or more tubes at a same time (which would not be possible if a cover must be closed afterwards), a facilitated setup during manufacture, and/or a shortfall of any need to add a sensor cover from a machine side.

As used herein, the term "disposable kit" may designate an entire kit or set structure as a whole, including disposables as the case may be, and the term "sensor" may designate a blood leakage detector (BLD) arranged to detect blood in e.g. a dialysate flow in a dialysis machine during an extracorporeal blood treatment.

More specifically, according to a first aspect of the present invention, there is provided a light shield to be arranged in a light shielding position with respect to a sensor or a blood leakage detector installed in a medical apparatus and monitoring for changes in transmittance of a translucent fluid carried in a tubing connected to the medical apparatus, wherein the light shield has a non-transparent configuration and is configured to prevent environmental light from being incident on a relevant detection active sensor area.

Preferably, the light shield is configured as a first light shield element formed in a block form of an elastomeric material and a size covering the relevant detection active sensor area, and having a clearance within in the block form arranged to accommodate the tubing carrying the fluid to be monitored by the sensor and/or the sensor itself.

Preferably, the block form is a first half block having a hollow as the clearance, and wherein the first half block is arranged to substantially symmetrically correspond to a second half block provided underneath the tubing, and arranged to be placed onto the second half block to thereby enclose and shield at least the detection active sensor area. It is noted that the sensor may be operatively incorporated into the second half block.

Preferably, the light shield is configured as a second light shield element formed of a non-transparent layer of a predetermined thickness and areal extension in at least an area where the detection active sensor area is underneath. It is understood that the second light shield element can be provided additionally or alternatively to the first light shield element.

Preferably the light shield is configured as a third light shield element formed of a non-transparent three-dimensional cavity in at least a region where the detection active sensor area is underneath. It is understood that the third light shield element can be provided additionally or alternatively to the first light shield element and/or the second light shield element.

Preferably, the third light shield element is a housing arranged to be open toward the sensor and/or to at least partially accommodate and/or surround the sensor.

Preferably, the light shield is configured as a fourth light shield element formed of a non-transparent coating or paint provided on the tubing at least over a region where the detection active sensor area is underneath. It is understood that the fourth light shield element can be provided additionally or alternatively to the first light shield element, the second light shield element and/or the third light shield element.

Preferably, the non-transparent coating or paint as the fourth light shielding element is formed into a H-shape or a][-shape arranged to extend onto side surfaces of a sensor holding mount and/or a sensor cover, the sensor cover being configurable as the first light shield element According to a second aspect of the invention, there is provided a disposable kit for a medical apparatus, the disposable kit being arranged to be mounted to the medical apparatus and to carry pre-installed disposables to be used during a medical treatment, comprising: a hard-shell subassembly arranged to be positioned in a region of the medical apparatus in the vicinity of a detection active sensor area of a sensor which is sensitive to light and installed in the medical apparatus; and at least one light shield element selected from the first to third light shield elements mentioned above, wherein the at least one light shield element is mounted to the hard-shell subassembly of the disposable kit in a region where the detection active sensor area is underneath.

Preferably, one of the pre-installed disposable components is a tubing carrying fluid to be monitored by the sensor, and the fourth light shield element mentioned above is provided to the tubing.

Preferably, the first light shield element, the second light shield element and/or the third light shield element as mentioned above is/are mounted to the hard shell as the at least one pre-installed component, and/or the fourth light shield element as mentioned above is provided to a tubing section being monitored by the sensor.

As used herein, devices, structures, configurations and/or components constituting the disposable kit for a medical apparatus and/or the sensor described and referred to herein may be configured to provide a variety of modifications, including more or less preinstalled configurations and/or separate parts to be put in proper place and connected upon operationally setting up the disposable kit and/or the sensor.

BRIEF DESCRIPTION OF THE DRAWINGS

The invention is best understood from the following detailed description when read in connection with the accompanying drawings. Included in the drawings are the following figures:

FIG. 2 schematically shows the light shield of FIG. 1 with a tubing section accommodated in the clearance and positioned with respect to a counterpart it is configured to cooperate with;

DETAILED DESCRIPTION OF THE PREFERRED EMBODIMENTS

Figure 1:
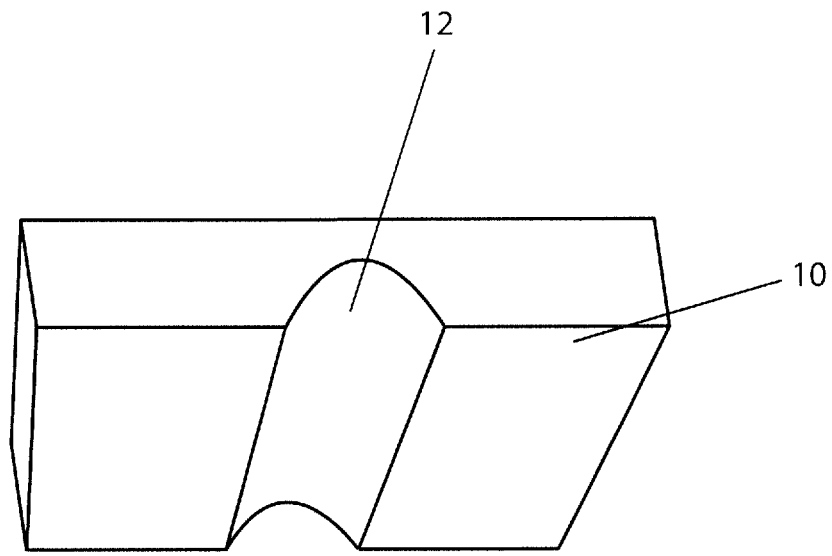
FIG. 1 schematically shows a perspective view of a light shield of a non-transparent material configured to a block form and having a clearance according to a first embodiment.

It is noted that similar or like parts visualized throughout the drawings and figures may be denoted by like reference numerals, and details thereof will not be described or explained redundantly. It is further noted that throughout the drawings and figures tubes and other components may be omitted or hidden in order to provide an improved vision.

FIG. 1 shows a perspective view of a light shield 10 of a non-transparent material, configured to a block form and having a clearance 12, which may be provided in the form of a groove, for example a substantially semi-circular groove, according to a first embodiment. The non-transparent material may for example consist of an (elastic and/or densely foamed) elastomeric material, a rubber or the like, and be colored to be preferably dark or black. Non-transparent or dense in here shall be understood to mean that the light shield 10 is impassable for incident light impinging thereon.

The light shield 10 may be of a substantially rectangular form of at least a size suitable to cover a light receiving area from top and sides, or detection active sensor area, of a sensor to be shielded against unwanted environmental light that might affect or influence the detection process and/or distort the detection or measurement carried out by the sensor.

It is noted that the sensor may be a detection device in a medical apparatus, and in particular, for example, a blood leakage detector (BLD) in an extracorporeal blood treatment apparatus such as a dialysis machine. It is further noted that an actual form of the light shield 10 put into practice is not limited to the rectangular form but may be any form or appearance suitable to sufficiently and effectively cover and shield the detection active area of the sensor so as to prevent environmental light from impinging thereon.

Figure 2:
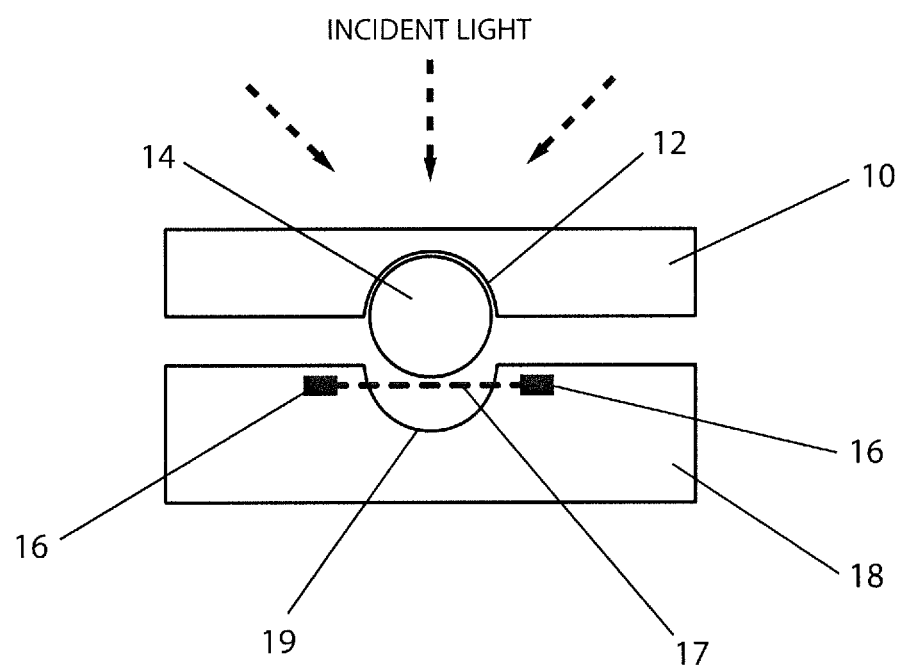

FIG. 2 schematically shows the light shield 10 of FIG. 1 with a tubing section 14 accommodated in the clearance and positioned with respect to a counterpart it is configured to cooperate with. As understood, the tubing section 14 forms part of a tube or fluid line flowing a translucent liquid to be monitored for changes in transmittance.

In the present embodiment, a blood leak or leakage detector (BLD) 16 for non-invasive blood leak detection is used as an example of the sensor. Such a detector may, without being limited thereto, comprise a mounting section comprising a solid body 18 with a U-shaped groove 19 for accommodating therein a tube or a fluid line in which a fluid to be monitored or measured flows. The solid body 18 may further comprise bores (not shown) via which the solid body 18 may be mounted, using e.g. screws, to a larger part such as the medical apparatus. A detection active area of the blood leak detector 18 may be arranged in the groove so as to be close to or in contact with the outer wall of the tube section, as schematically illustrated in FIG. 2 by a dashed line between a left side and a right side sensor part. It is noted that, as at least part of the detection active area, one of the left and right sensor parts may form a light sender arranged to emit detection light 17 into the groove 19 and toward the tubing section 14, and the respective other one of the left and right sensor parts may form a light receiver arranged to receive detection light 17 having passed through the groove 19 and the tubing section 14, respectively. The detection active area may be connected to a sensor electronic circuit via a cable or lead, both being not shown, exiting from a rear side of the solid body 18.

Such a blood leak detector (BLD) may be a non-invasive optical sensor to detect smallest amounts of blood in clear fluids on transparent plastic tubing. As blood should in e.g. a dialysis machine not cross the blood/dialysate membrane, dialysis machines are usually equipped with a detector to monitor blood leaks. The optical sensor uses a light source with a wavelength optimized toward sensitivity regarding the detection of specific colors of fluid (e.g. red blood cells diluted in dialysate). A threshold may trigger an alarm if the amount of blood in the fluid exceeds a predetermined limit. The blood leakage detector is as such a known component and will therefore not be described herein in further detail.

In the present embodiment, the light shield 10 may have a block form which is a first half block having a hollow as the clearance 12. This first half block may be arranged to substantially symmetrically correspond to a second half block (e.g. the solid body of the blood leakage detector mentioned above) provided underneath the tubing 14, and arranged to be placed onto the second half block to thereby more fully enclose and shield at least the detection active sensor area against incident ambient or environmental light.

In particular, the light shield 10 may be pre-installed, in other words fixed, in a predetermined position to a plate-like part of a disposable kit or, in a preferred embodiment directly to the tubing section 14, so that the light shield 10 (i.e. the first half block) is automatically placed on the sensor counterpart (i.e. the second half block) and automatically and without any further manual steps provides its light shielding effect upon mounting the disposable kit or the tubing section 14 directly supporting the light shield 10 to its predetermined location on the medical apparatus.

Figure 3:
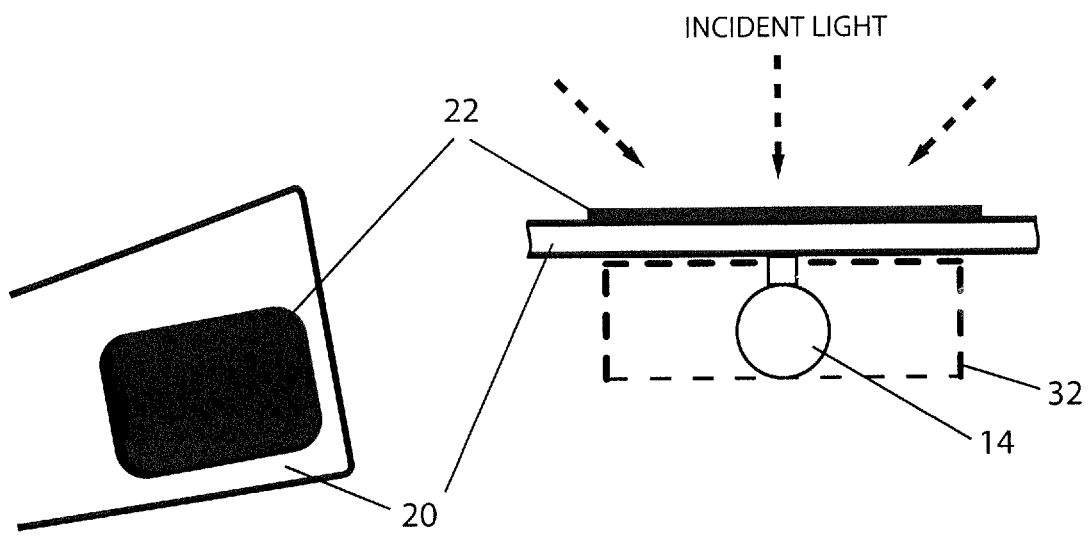
FIG. 3 schematically shows a plan view and a side view of a hard-shell section as forming part of a disposable kit and a light shield configured as a flat layer as a second embodiment or a box-like housing as a third embodiment, made of a non-transparent material and attached to the hard-shell section.

As a second embodiment, FIG. 3 shows a plan view and a side view of a plate-like hard-shell 20 section forming part of a disposable kit (not further shown) and a light shield configured as a flat layer 22 made of a non-transparent material and attached to the hard-shell 20 section.

A more detailed description on one possible configuration of the disposable kit is given in US 2010/0094192 A, the disclosure of which is incorporated by reference.

In other words, the disposable kit may comprise a shell like outer appearance, based on e.g. one or more plate-like elements made of for example a plastics material. In order to improve visibility of disposable components internal to the disposable kit in the mounted state thereof, the plate-like elements may be translucent or opaque as well, i.e. not immediately prevent light from passing through them by themselves.

In such cases, the flat layer 22 light shield may be mounted to the plate-like element at least in a region where the sensor or its detection active area is located underneath. It is understood that the flat layer 22 light shield element may be equipped additionally or alternatively (solely) to the light shield 10 of the first embodiment. When provided additionally, the shielding effect of the flat layer 22 light shield can advantageously add to the protection achieved by the light shield 10 if the area covered by the flat layer 22 light shield is larger to a certain extent than the surface area of the light shield 10, for example in cases where the light shield 10 is erroneously not correctly installed in place.

As a third embodiment, the light shield may be modified to be a box-like casing 32 or housing which may have a base or bottom and be at least partially open at the opposing side. FIG. 3 shows the casing 32 in its right part in dashed lines. The casing 32 or housing may in this case be mounted at its bottom to the plate-like hard-shell element 20 of the disposable kit such that its open side opens toward the sensor and thus can automatically and without any further manual steps surround or enclose the sensor from all outer sides when the disposable kit is mounted to the medical apparatus.

At least partially open as mentioned above means that it may be sufficient that the side of the casing 32 opposed to the bottom is partially closed and has only a smaller opening of approximately the size or circumference of the sensor or light shield 10. In such a configuration, the sensor or light shield 10 can be sort of inserted into the smaller opening with the casing 32 enclosing it more tightly, which can advantageously further improve the shielding effect against stray light entering sideways. In addition, a seal may be additionally provided around the opening and further enhance the aforementioned effects.

It is understood that the configurations of the second and third embodiments may be applied additionally or alternatively to the first embodiment, i.e. with or without the use of the light shield 10. Also, it is understood that the second and the third embodiment may be combined, i.e. both the flat layer 22 light shield and the casing 32 may be provided at the plate-like element of the disposable kit.

Figure 4:
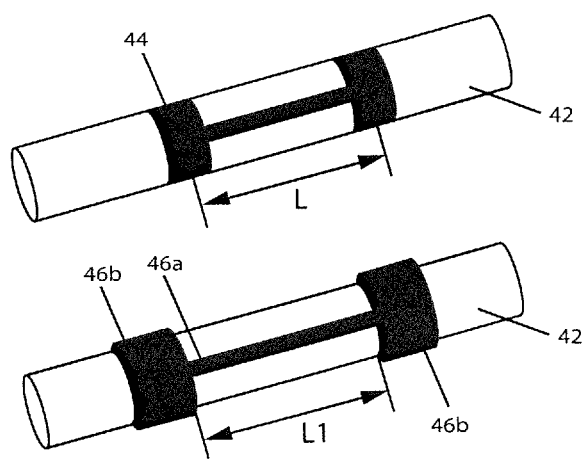
FIG. 4 schematically shows a view of a tubing section having a light shield configured as a coating or a paint according to a fourth embodiment.

FIG. 4 schematically shows a view of a tubing section 42 having a light shield configured as a coating or a paint 44, 46*a*, 46*b* according to a fourth embodiment.

Because the tubing 42 diameter may be large to an extent that block light shields as described with respect to FIGS. 1 and 2, i.e. the light shield 10 and the BLD sensor housing or second block 18, cannot contact each other and thus cannot completely enclose and shield the tubing 42 themselves, in order to better protect the sensor or its detection active area from ambient light or stray light entering laterally or sideways in e.g. flat angles, the coating or paint 44, 46*a*, 46*b* may be applied directly onto the outer wall of a tube section 42 of at least a length sufficiently exceeding the detection active area of the sensor and/or the block light shield 10 and the BLD sensor housing or second block 18.

For example, as shown in FIG. 4, the coating or paint light shield 44 may be provided in a H-form or a][-Form and arranged to cover the tube section 42 along a length greater than a length L of the block light shield so as to prevent ambient light from entering into the tube section 42 on a larger length and to finally keep it away from the detection active area of the sensor. The H or][ is generally preferable because the BLD sensor requires light to pass through the tubing 42. Thus, the H- or][-Form is advantageously configurable to both provide a light path through the tubing 42 where necessary and a non-transparent shield on tubing sections not forming part of the light path.

In a modification of the fourth embodiment, the coating or paint light shield 46*a*, 46*b* may be provided as covering the tubing 42 not with substantially constant thickness but as a thinner coating or paint 46*a* along a length L1 the tubing 42 runs within the block light shield, and covering a further part of the tubing 42 at both sides of the block light shield as a thicker coating or paint 46*b*. As an example, the coating or paint light shield 44, 46*a*, 46*b* may consist of either printing on tubing 42 top as wide as the sensor gap on the outer diameter.

In a further modification of the fourth embodiment, the paint or coating sections 46*b* may be provided as being stepped in their lateral extension so that a predetermined length of the paint or coating sections 46*b* has substantially the same thickness as the inner paint or coating section 46*a* interconnecting the sections 46*b*, and the remaining length of the paint or coating sections 46*b*, i.e. the length outside the block light shields in a mounted state, has a thicker thickness.

It is noted that the non-transparent coating may for example be a pre-formed component arranged to be shiftable and/or shrinkable onto the tubing 42 hose a wrapping wound around the tubing 42, or the like for covering also the side areas of the tubing 42 where optical path of the sensor is not affected or touched.

In addition, it is understood that the configuration of the fourth embodiment may be applied additionally or alternatively to the light shield according to the first embodiment, the second embodiment and/or the third embodiment.

As has been described above, in some configurations a component is mounted on the disposable kit so that after the disposable kit is loaded the component will cover the sensor. The component can consist of a non-transparent area on a disposable kit plate itself, and/or a cover section (internal cover housing) inside disposable kit.

In line therewith, a light shield is arranged in a light shielding position with respect to a sensor or a blood leakage detector installed in a medical apparatus and monitoring for changes of transmittance in a translucent fluid carried in a tubing connected to the medical apparatus. The light shield has a non-transparent configuration and is configured to prevent environmental light from being incident on a relevant detection active sensor area. Further, a disposable kit for a medical apparatus which is arranged to be mounted to the medical apparatus and to carry pre-installed disposables to be used during a medical treatment comprises a hard-shell subassembly arranged to be positioned in a region of the medical apparatus in the vicinity of a detection active sensor area of a sensor which is sensitive to light and installed in the medical apparatus. At least one light shield element is selected from first to third light shield elements, and the at least one light shield element is mounted to the hard-shell subassembly of the disposable kit in a region where the detection active sensor area is underneath.

Although specific amounts such as weight, absolute length, width and thickness, coloring, form and minor details of an overall light shield and disposable kit are not shown, such specifications are within the purview of the invention described hereinabove as will be understood to those skilled in the art. It is also to be understood that the specific text, sequence and content of configurations and components shown in the drawing and described herein are by way of illustration and example only and the apparatus, system and operation thereof are not to be limited thereby.

Therefore and as understood, the invention is not limited to the described preferred embodiment and modifications thereof, and combinations of at least parts of the embodiment, modifications and equivalents all within the scope defined by the appended claims may occur to the skilled person.

The invention claimed is:

1. A light shield to be arranged in a light shielding position with respect to a sensor or a blood leakage detector, the sensor or blood leakage detector being installed in a medical apparatus and monitoring for changes in transmittance of a translucent fluid, the light shield comprising:
   a tubing connected to the medical apparatus and configured to carry the translucent fluid;
   a first light shield element formed of non-transparent paint provided on the tubing at least over a region of the tubing with an active sensor detection area underneath;
   wherein the light shield has a non-transparent configuration and is configured to prevent environmental light from being incident on the active sensor detection area.

2. The light shield according to claim 1, wherein the light shield further comprises:
   a second light shield element formed in a block form of an elastomeric material and of a size covering the active sensor detection area, and having a clearance within the block form arranged to accommodate the tubing carrying the translucent fluid to be monitored by the sensor or the blood leakage detector.

3. The light shield according to claim 2, wherein the block form is a first half block having a hollow as the clearance, and wherein the first half block is arranged to substantially symmetrically correspond to a second half block provided underneath the tubing and is arranged to be placed onto the second half block to enclose and shield at least the active sensor detector area.

4. The light shield according to claim 2, wherein the block form is further arranged to accommodate the sensor or the blood leakage detector.

5. A disposable kit for a medical apparatus, the disposable kit being configured to be mounted to the medical apparatus and to carry pre-installed disposable components to be used during a medical treatment, the disposable kit comprising:
   a hard-shell subassembly arranged to be positioned in a region of the medical apparatus in the vicinity of an active sensor detection area of a sensor which is sensitive to light and installed in the medical apparatus; and
   at least one light shield according to claim 2, each of the at least one light shield including the second light shield element;
   wherein the at least one second light shield element is mounted to the hard-shell subassembly of the disposable kit in a region where the active sensor detection area is underneath, and
   wherein one of the pre-installed disposable components is the tubing carrying fluid to be monitored by the sensor or the blood detector, and the first light shield element is formed on the tubing.

6. The disposable kit for a medical apparatus according to claim 5, wherein the at least one second light shield element is mounted to the hard shell as the at least one pre-installed component.

7. The disposable kit for a medical apparatus according to claim 6, wherein the first light shield element is formed on a section of the tubing being monitored by the sensor or the blood detector.

8. The disposable kit for a medical apparatus according to claim 5, wherein the first light shield element is formed on a section of the tubing being monitored by the sensor or the blood detector.

9. The light shield according to claim 1, wherein the light shield further comprises:
   a second light shield element formed of a non-transparent layer of a predetermined thickness and areal extension in at least an area where the active sensor detector area is underneath.

10. The light shield according to claim 1, wherein the light shield further comprises:
    a second light shield element formed of a non-transparent three-dimensional cavity in at least a region where the active sensor detection area is underneath.

11. The light shield according to claim 10, wherein the second light shield element is a casing arranged to be at least one of (1) open toward the sensor or the blood leakage detector, (2) at least partially accommodate the sensor or the blood leakage detector, or (3) surround the sensor or the blood leakage detector.

12. The light shield according to claim 1, wherein the non-transparent paint is formed into an H-shape arranged to extend onto side surfaces of at least one of a sensor holding mount or a sensor cover.

13. A light shield to be arranged in a light shielding position with respect to a sensor or a blood leakage detector, the sensor or blood leakage detector being installed in a medical apparatus and monitoring for changes in transmittance of a translucent fluid, the light shield comprising:
    a tubing connected to the medical apparatus and configured to carry the translucent fluid;
    a first light shield element formed of non-transparent coating adhered directly to an outer wall of the tubing at least over a region of the tubing with an active sensor detection area underneath;
    wherein the light shield has a non-transparent configuration and is configured to prevent environmental light from being incident on the active sensor detection area.

14. The light shield of claim 13, wherein the coating comprises a sticker.

* * * * *